United States Patent [19]

Marchi et al.

[11] Patent Number: 5,496,807
[45] Date of Patent: Mar. 5, 1996

[54] METHOD OF TREATMENT OF DIABETIC NEPHROPATHY BY MEANS OF SULODEXIDE OF MEDICINES CONTAINING IT

[75] Inventors: Egidio Marchi; Gianfranco Tamagnone, both of Bologna, Italy

[73] Assignee: Alfa Wassermann S.p.A., Pescara, Italy

[21] Appl. No.: 227,502

[22] Filed: Apr. 14, 1994

[30] Foreign Application Priority Data

May 10, 1993 [IT] Italy ................... BO93A0205

[51] Int. Cl.$^6$ ..................... A61K 31/70; A61K 31/69
[52] U.S. Cl. ................................ 514/52; 514/64
[58] Field of Search ........................... 514/52, 64

[56] References Cited

U.S. PATENT DOCUMENTS 5,252,339  10/1993  Cristofori et al. ................ 424/479

OTHER PUBLICATIONS

Chemical Abstracts 120:51646u (1994) Abstracting a 1993 reference.

Primary Examiner—Jerome D. Goldberg
Attorney, Agent, or Firm—Bucknam and Archer

[57] ABSTRACT

The use of sulodexide, a glycosaminoglycan of natural origin extracted from mammalian intestinal mucosa, and of medicines containing it in the treatment of patients suffering from nephropathy of diabetic origin constitutes the object of the present invention. The effectiveness of sulodexide has been shown by the significative decrease of the albuminuria in microalbuminuric and macroalbuminuric diabetic patients treated with pharmaceutical compositions administered by oral or intramuscular route containing therapeutically effective amounts of drug.

4 Claims, No Drawings

METHOD OF TREATMENT OF DIABETIC NEPHROPATHY BY MEANS OF SULODEXIDE OF MEDICINES CONTAINING IT

BACKGROUND OF THE INVENTION

The use of glycosaminoglycans, and particularly of heparins, in anticoagulant and antithrombotic therapies is well known.

Sulodexide is a glycosaminoglycan of natural origin, extracted from mammalian intestinal mucosa, possessing a sulfation degree and an anticoagulant activity lower than those of heparin, as shown by Radhakrishnamurthy B. et at., *Atherosclerosis*, 31, 217–229, (1978). It is marketed under the trademark VESSEL DUE F® for the treatment of vascular pathologies with thrombotic risk like periferal arteriopathies, as shown by Crepaldi G. et al., *Atherosclerosis*, 81, 233, (1990), cardiovasculopathies, as shown by Tramarin R. et al., *Medical Praxis*, 8, 1, (1987), cerebrovasculopathies, as shown by Sozzi C., *Eur. Rev. Med. Pharmacol. Sci.*, 6, 295, (1984) and venous pathologies of the lower limbs, as shown by Cospite M. et al., *Acta Therapeutica*, 18, 149, (1992).

Kanwar Y. S. et al., *Sem. Nephrol.*, 5, 307, (1985) and Groggel G. C. et al., *Kidney Int.*, 33, 517, (1988), recently produced evidence of the probable role of glycosaminoglycans in helping the integrity and the functioning of the renal cells.

Moreover, Canfield J. P. et at., *Lab. Invest.*, 39, 505, (1978), previously showed a decrease of glycosaminoglycans of membrane in many conditions of nephropathy, while Baggio B. et al., *Nephron.*, 43, 187, (1986) showed this decrease through an increased urinary elimination of glycosaminoglycans in diabetic, non-albuminuric, patients. This increased excretion of glycosaminoglycans in diabetic nephropathies, shown also by Partasarathy N. et al., *Diabetes*, 31, 738, (1982), recently suggested to Gambaro G. et al., *Metabolism*, 38, 419, (1989), the possibility of resorting to the determination of the amount of glycosaminoglycans excreted by urinary route as an analytical method more reliable than the microalbuminuria in the recognition of the nephropathy of diabetic origin.

Lastly, Diamond J. R. et al., *Renal Physiol.*, 9, 366, (1986) and Parkerson M. B. et al, *J. Clin. Invest.*, 81, 69, (1988), showed in animals the potential protective effect of heparin and its derivatives in models of experimental nephropathy not related to diabetic nephropathy, like chronic nephrosis from aminoglycosides and renal pathologies resulting from the subtotal renal ablation in the rat.

Lastly, the possibility to use heparin, low molecular weight heparin fractions, chemically modified heparins or low molecular weight dermatan sulfate in the treatment of the diabetic nephropathy and neuropathy has been described in the European patent publication EP 0513513. This possibility of therapeutic use was shown by means of pharmacological tests on animals: diabetes was caused by streptozotocin in Sprague Dawley male albino rats and the diabetic rats were treated with the above mentioned glycosaminoglycans whose effectiveness was determined on the basis of some parameters like the diminution of the albuminuria and of the thickness of the basal glomerular membrane and the increase of the glomerular anionic charges.

SUMMARY OF THE INVENTION

The therapeutic use of sulodexide, a glycosaminoglycan of natural origin extracted from mammalian intestinal mucosa possessing a sulfation degree and an anticoagulant activity lower than those of heparin, and of the medicines containing it in the treatment of patients suffering from microalbuminuria or macroalbuminuria, i.e. showing a more or less substantial increase of albumin in the urines, until 200 mcg/min for the microalbuminuric patients and more than 200 mcg/min for the macroalbuminuric patients, constitutes the object of the present invention. The present invention amounts to overcoming of the teachings of the prior art because a true therapeutic effectiveness on man of a drug widely used for a long period of time in pathologies completely different from the nephropathy of diabetic origin has been clinically demonstrated.

This pathology affects from 30% to 40% of the patients suffering from insulin dependent type I diabetes and causes in time a chronic renal insufficiency that often obliges the patient to submit himself to the dialysis treatment.

The diabetic nephropathy is a clinically well defined pathology characterized by proteinuria, hypertension, edema and renal insufficiency and generally occurs in patients suffering from diabetes from more than ten years. The diabetic nephropathy differentiates in three types, on the basis of the histopathologic characteristics that distinguish it: 1) glomerulosclerosis, 2) modification of the vascular structure, mainly in the small arterioles and 3) tubulointerstitial disease.

The more characteristic aspect of the diabetic nephropathy is the glomerular injury, detectable by the enlargement of the mesangium and by the thickening of the basal membrane, which often looks like a diffuse cicatrization of the whole glomerule.

The first clinical evidence of the diabetic nephropathy is given by the presence of albuminuria in the urines, albuminuria that takes the name of microalbuminuria when the albumin amount in the urines is comprised between 20 and 200 mcg/min and of macroalbuminuria when this amount exceeds 200 mcg/min.

The therapeutic protections used at present for the treatment of diabetic patients with complications of albuminuria and nephropathy are:

1) Use of ACE-inhibitors antihypertensive drugs;
2) Control of glycemic values;
3) Lypoproteic diet.

No drug, till now, has been able to lower in a substantial way the levels of albuminuria in diabetic patients and only the ACE-inhibitors drugs have given encouraging results.

It has now been found that the administration of pharmaceutical compositions containing therapeutically effective amounts of sulodexide to diabetic patients with microalbuminuria or macroalbuminuria causes a remarkable and significative lowering in the urinary excretion of albumin. Moreover it has been ascertained that the treatment with sulodexide allowed to keep substantially unchanged the renal functioning also four months after the cessation of the treatment as the glomerular filtrate, measured before the beginning of the treatment with sulodexide and four months after the end of the treatment, remained substantially unchanged.

All kinds of pharmaceutical compositions administrable by oral, subcutaneous, intramuscular or intravenous routes can be advantageously used in carrying out the present invention. Tablets, controlled release tablets, gastroresistant tablets, capsules, gastroresistant capsules, granulates or syrups are the pharmaceutical compositions administrable by oral route preferred in the realization of the present invention.

The dosage, function of the body weight and the seriousness of the pathology, is comprised between 500 L.R.U. (lipoprotein lipase releasing units) and 1500 L.R.U. a day.

The therapeutical effectiveness of sulodexide has been evaluated in two clinical studies. The first test was carried out on ten ambosexual diabetic patients, partly microalbuminuric and partly macroalbuminuric, to whom 1000 L.R.U. of sulodexide a day were administered for 60 consecutive days under form of two 250 L.R.U. capsules administered twice a day of VESSEL DUE F®.

The diabetic patients continued the pre-existent antihypertensive therapy based on calcium-antagonist and/or ACE-inhibitor drugs throughout the treatment with sulodexide.

The therapeutic results of the treatment with sulodexide, reported in example 1, show how 8 out of 10 diabetic patients, 4 microalbuminuric and 4 macroalbuminuric, obtained a significative lowering in the albumin excretion, with an average decrease respectively equal to 44% and 35% and how only two microalbuminuric patients did not get any improvement. Moreover no substantial change of the glomerular renal filtrate was noted four months after the end of the treatment with sulodexide. This fact shows how the treatment with sulodexide made possible to keep substantially unaltered the renal functionality for a medium period of time after the end of the treatment.

The second clinical test was carried out on five ambosexual diabetic patients, three microalbuminuric and two macroalbuminuric, to whom 600 L.R.U. of sulodexide a day were administered by intramuscular route for 21 consecutive days under form of one 600 L.R.U. vial of VESSEL DUE F®. The diabetic patients continued the pre-existent antihypertensive therapy based on calcium-antagonist and/or ACE-inhibitor drugs throughout the treatment with sulodexide. The therapeutic results of the treatment with sulodexide, reported in example 2, show a significative lowering in the albumin excretion of all the five patients.

The examples of clinical tests are given to further illustrate the invention and cannot be taken as a limitation of the invention itself.

EXAMPLE 1

Treatment of nephropathic diabetic patients with capsules containing sulodexide

Ten ambosexual adult consenting diabetic patients, six with microalbuminuria and four with macroalbuminuria, were treated with sulodexide at the Institute of Internal Medicine of the University of Padua. The albuminuria of the ten patients was evaluated every day for three days before the beginning of the treatment with sulodexide and its average value was calculated; also the value of the glomerular filtrate was assessed. Then two 250 L.R.U. capsules of VESSEL DUE F® were given to the patients twice a day for 60 consecutive days while keeping the pre-existent antihypertensive therapy based on calcium-antagonist and/or ACE-inhibitor drugs for the whole time.

The albuminuria was evaluated again at the end of the therapy while the value of the glomerular filtrate was assessed again four months after the end of the treatment in order to verify the renal functionality.

The clinical results showing the effectiveness of the treatment with sulodexide are summarized in the following three tables. Table 1 refers to all the microalbuminuric patients, table 2 refers to patients who favourably responded to the treatment with sulodexide and table 3 refers to macroalbuminuric patients.

TABLE 1

| Patient | Sex | Age (years) | Weight (Kg) | Antihypertensive therapy | Albumin before the treatment (mcg/min) | Albumin after 60 days of treatment (mcg/min) | Glomerular filtration before the treatment (ml/min) | Glomerular filtration four months after the end of the treatment (ml/min) |
|---|---|---|---|---|---|---|---|---|
| 1 | M | 54 | 66 | Calcium-antagonist drugs | 59.17 | 86.00 | 106.34 | 106.00 |
| 2 | M | 50 | 104 | Calcium-antagonist plus ACE-inhibitor drugs | 199.82 | 81.77 | 121.00 | 125.80 |
| 3 | M | 60 | 95 | ACE-inhibitor drugs | 98.86 | 86.12 | 98.57 | 102.30 |
| 4 | F | 40 | 76 | Calcium-antagonist plus ACE-inhibitor drugs | 65.55 | 114.98 | 86.00 | 90.60 |
| 5 | M | 48 | 76 | Calcium-antagonist drugs | 47.82 | 33.10 | 86.56 | 85.54 |
| 6 | F | 49 | 78 | Calcium-antagonist plus ACE-inhibitor drugs | 44.60 | 20.40 | 121.70 | 119.6 |
| Average $\bar{X} \pm$ s.e. | | 50.1 ± 2.6 | 82.5 ± 5.6 | | 85.9 ± 23.6 | 70.3 ± 14.4 | 103.3 ± 6.3 | 104.9 ± 6.2 |

TABLE 2

| Patient | Sex | Age (years) | Weight (Kg) | Antihypertensive Therapy | Albumin before the treatment (mcg/min) | Albumin after 60 days of the treatment (mcg/min) |
|---|---|---|---|---|---|---|
| 2 | M | 50 | 104 | Calcium-antagonist plus ACE-inhibitor drugs | 199.82 | 81.77 |
| 3 | M | 60 | 95 | ACE-inhibitor drugs | 98.86 | 86.12 |
| 5 | M | 48 | 76 | Calcium-antagonist drugs | 47.82 | 33.10 |
| 6 | F | 49 | 78 | Calcium-antagonist plus ACE-inhibitor drugs | 44.60 | 20.40 |
| Average $\overline{X} \pm$ s.e. | | 51.7 ± 2.7 | 88.2 ± 6.7 | | 97.7 ± 18.1 | 55.3 ± 16.7 |

TABLE 3

| Patient | Sex | Age (years) | Weight (Kg) | Antihypertensive therapy | Albumin before the treatment (mcg/min) | Albumin after 60 days of treatment (mcg/min) | Glomerular filtration before the treatment (ml/min) | Glomerular filtration four months after the end of the treatment |
|---|---|---|---|---|---|---|---|---|
| 7 | F | 63 | 81 | Calcium-antagonist drugs | 307.63 | 205.97 | 72.28 | 71.24 |
| 8 | M | 39 | 63 | Calcium-antagonist drugs | 2402.78 | 1215.28 | 94.42 | 70.80 |
| 9 | F | 69 | 85 | Calcium-antagonist plus ACE-inhibitor drugs | 416.67 | 135.85 | 72.58 | 68.31 |
| 10 | F | 44 | 81 | Calcium-antagonist plus ACE-inhibitor drugs | 1564.01 | 1493.06 | 52.48 | 55.32 |
| Average $\overline{X} \pm$ s.e. | | 53.7 ± 7.2 | 77.5 ± 4.9 | | 1172.76 ± 249.4 | 762.5 ± 346.5 | 72.9 ± 8.5 | 66.4 ± 3.75 |

EXAMPLE 2

Treatment of nephropathic diabetic patients by intramuscular route with vials containing sulodexide Five ambosexual adult consenting diabetic patients, three with microalbuminuria and two with macroalbuminuria, were treated with sulodexide at the Institute of Internal Medicine of the University of Padua.

The albuminuria of the five patients was evaluated every day for three days before the beginning of the treatment with sulodexide and its average value was calculated.

One vial of VESSEL DUE F®, containing in 2 ml of solution 600 L.R.U. of sulodexide, was given by intramuscular route to the patients for 21 consecutive days while keeping the pre-existent antihypertensive therapy based on calciumantagonist and/or ACE-inhibitor drugs far the whole time.

At the end of the therapy the albuminuria was evaluated again and the clinical results showing a significant decrease of the albuminuria, from 42.86% to 94.72%, are summarized in the following table 4.

TABLE 4

| Patient | Sex | Age (years) | Weight (Kg) | Antihypertensive Therapy | Albumin before the treatment (mcg/min) | Albumin after 21 days of the treatment (mcg/min) |
|---|---|---|---|---|---|---|
| 1 | F | 65 | 63 | Calcium-antagonist drugs | 30.90 | 15.28 |
| 2 | F | 23 | 71 | No antihypertensive therapy | 31.60 | 1.67 |
| 3 | F | 40 | 76 | calcium-antagonist plus ACE-inhibitor drugs | 99.40 | 56.80 |
| 4 | M | 53 | 100 | Calcium-antagonist drugs | 639.93 | 324.38 |
| 5 | F | 44 | 81 | Calcium-antagonist plus ACE-inhibitor drugs | 2222.20 | 346.25 |
| Average $\overline{X} \pm$ s.e. | | 45 ± 7 | 78.2 ± 6.2 | | 604.81 ± 420.15 | 148.88 ± 76.73 |

We claim:

1. A method of treatment of diabetic nephropathy which consists of administering to a living subject affected by diabetic nephropathy, said living subject exhibiting microalbuminuria or macroalbuminuria, a therapeutically effective amount of sulodexide.

2. The method according to claim 1 wherein the amount of sulodexide is comprised between 500 L.R.U. and 1500 L.R.U..

3. The method according to claim 1, wherein sulodexide is administered by oral route.

4. The method according to claim 1, wherein sulodexide is administered by subcutaneous, intramuscular or intravenous route.

* * * * *